(12) United States Patent
Sugita et al.

(10) Patent No.: US 10,605,748 B2
(45) Date of Patent: Mar. 31, 2020

(54) X-RAY INSPECTION APPARATUS AND X-RAY INSPECTION METHOD

(71) Applicant: OMRON Corporation, Kyoto-shi, Kyoto (JP)

(72) Inventors: Shinji Sugita, Kyoto (JP); Yuji Umemoto, Osaka (JP); Takako Onishi, Kyotanabe (JP)

(73) Assignee: OMRON Corporation, Kyoto-shi (JP)

( * ) Notice: Subject to any disclaimer, the term of this patent is extended or adjusted under 35 U.S.C. 154(b) by 312 days.

(21) Appl. No.: 15/603,573

(22) Filed: May 24, 2017

(65) Prior Publication Data

US 2017/0356859 A1 Dec. 14, 2017

(30) Foreign Application Priority Data

Jun. 13, 2016 (JP) .................. 2016-117187

(51) Int. Cl.
*G01N 23/04* (2018.01)
*G01N 23/046* (2018.01)

(52) U.S. Cl.
CPC ........... *G01N 23/04* (2013.01); *G01N 23/046* (2013.01); *G01N 2223/3303* (2013.01)

(58) Field of Classification Search
None
See application file for complete search history.

(56) References Cited

U.S. PATENT DOCUMENTS

| 4,136,388 A | 1/1979 | Lindquist |
| 4,803,639 A | 2/1989 | Steele et al. |
| 7,857,513 B2 | 12/2010 | Li |
| 2008/0226035 A1 | 9/2008 | Masuda et al. |
| 2010/0172561 A1 | 7/2010 | Ota et al. |

(Continued)

FOREIGN PATENT DOCUMENTS

| CN | 101266218 A | 9/2008 |
| CN | 101776618 A | 7/2010 |

(Continued)

OTHER PUBLICATIONS

The extended European search report dated Sep. 14, 2017 in the counterpart European patent application.

(Continued)

*Primary Examiner* — Hoon K Song
(74) *Attorney, Agent, or Firm* — Metrolex IP Law Group, PLLC (57) ABSTRACT

An X-ray inspection apparatus includes a stage that moves an inspection object, an X-ray source, and/or an X-ray camera by driving a motor, a position detection unit that periodically obtains a position detection value of the motor, and stores the value in association with time, an imaging timing obtaining unit that stores an imaging timing at which imaging is performed by the X-ray camera in association with time, an imaging position calculation unit that calculates relative positions of the inspection object, and the X-ray source and the X-ray camera corresponding to the imaging timing using the position detection value of the motor at the imaging timing, and a reconstruction unit that performs reconstruction using image data captured by the X-ray camera and the relative positions in the image data at the imaging timing.

7 Claims, 8 Drawing Sheets

(56) References Cited

U.S. PATENT DOCUMENTS

| | | | |
|---|---|---|---|
| 2012/0076260 A1* | 3/2012 | Kitagawa | A61B 6/022 378/41 |
| 2015/0332485 A1* | 11/2015 | Klausz | G06T 11/006 378/8 |
| 2016/0189400 A1 | 6/2016 | Li et al. | |
| 2019/0197741 A1* | 6/2019 | Nishii | A61B 6/025 |

FOREIGN PATENT DOCUMENTS

| | | |
|---|---|---|
| CN | 102419793 A | 4/2012 |
| CN | 104599299 A | 5/2015 |
| JP | S54-47494 A | 4/1979 |
| JP | H1-305345 A | 12/1989 |
| JP | 2002-131246 A | 5/2002 |
| JP | 2014-115216 A | 6/2014 |

OTHER PUBLICATIONS

The Office Action dated Oct. 9, 2018 in a counterpart Japanese patent application.
Office action dated Jan. 22, 2018 in a counterpart European Patent application.

* cited by examiner

Input imaging instruction for first image: X-ray source (200, 200); camera (50, 50)

| Time (401) | X-ray source X-axis (402) | X-ray source Y-axis (403) | Camera X-axis (404) | Camera Y-axis (405) | Camera imaging flag (406) |
|---|---|---|---|---|---|
| 1 | 100 | 100 | 100 | 100 | OFF |
| 2 | 120 | 125 | 90 | 90 | OFF |
| 3 | 150 | 160 | 75 | 75 | OFF |
| 4 | 180 | 185 | 65 | 68 | OFF |
| 5 | 195 | 190 | 55 | 53 | OFF |
| 6 | 210 | 205 | 45 | 52 | ON |
| 7 | 230 | 220 | 40 | 45 | OFF |
| 8 | 250 | 240 | 30 | 40 | OFF |
| ... | ... | ... | ... | ... | ... |

Imaging real coordinates for first image: X-ray source (210, 205), camera (45, 52)

Second image

FIG. 5A

Imaging flag ON at imaging start

| Time | Coor-dinate | ... | Imaging flag |
|---|---|---|---|
| 1 | | | OFF |
| 2 | | | OFF |
| 3 | | | ON |
| 4 | | | OFF |
| 5 | | | OFF |
| 6 | | | OFF |
| ... | | | ... |

Average coordinates from ON to (ON + exposure time)

FIG. 5B

Imaging flag ON at imaging end

| Time | Coor-dinate | ... | Imaging flag |
|---|---|---|---|
| 1 | | | OFF |
| 2 | | | OFF |
| 3 | | | OFF |
| 4 | | | OFF |
| 5 | | | ON |
| 6 | | | OFF |
| ... | | | ... |

Average coordinates from (ON - exposure time) to ON

FIG. 5C

Imaging flag ON during exposure

| Time | Coor-dinate | ... | Imaging flag |
|---|---|---|---|
| 1 | | | OFF |
| 2 | | | OFF |
| 3 | | | ON |
| 4 | | | ON |
| 5 | | | ON |
| 6 | | | OFF |
| ... | | | ... |

Average coordinates during ON

X-RAY INSPECTION APPARATUS AND X-RAY INSPECTION METHOD

CROSS REFERENCE TO RELATED APPLICATIONS

This application claims priority from prior Japanese Patent Application No. 2016-117187 filed with the Japan Patent Office on Jun. 13, 2016, the entire contents of which are incorporated herein by reference.

FIELD

The present disclosure relates to an X-ray inspection technique for capturing multiple images of an inspection object using X-rays and generating three-dimensional data for the object.

BACKGROUND

Techniques such as tomosynthesis and computed tomography (CT) are used for generating three-dimensional data from multiple X-ray images. Both these techniques should use accurate imaging positions in reconstructing the data. Any inaccurate positions for imaging, or mismatch between intended imaging positions and actual imaging positions, can lower the quality of the three-dimensional data.

Inaccurate imaging positions are caused by less accurate positioning of the stages that move an X-ray source, a camera, and an inspection object.

Producing higher-resolution images needs higher positioning accuracy. In the technical field involving increasingly smaller electronic components, for example, the imaging operation may be performed at a resolution as high as several micrometers. In such imaging, any less accurate positioning can lower the image quality for the reasons described below.

Under the same positioning accuracy, the quality of an image is affected more as the image has a higher resolution. This is because a positioning error creates a larger deviation in an image with a higher resolution. Additionally, the field of view is narrower (or the imaging area is smaller) for an image with a higher resolution, increasing the number of images to be captured. To shorten the time taken for the inspection, the stages are to be moved at high speed. Moving the stages at high speed can lower the positioning accuracy further.

Although the stages may be improved to increase the positioning accuracy, such improvement will increase the cost. Another possible solution may be to reconstruct the data after correcting the imaging position to an accurate position.

Preliminary learning a deviation between a target position and an actual position and correcting the imaging position based on the learning result is not effective. This is because the same deviation may not occur, and the deviation can vary in every imaging operation (due to repeatability error).

Patent Literature 1 describes a technique for calculating a positional deviation using values read during imaging by a sensor that is installed on a stage. More specifically, Patent Literature 1 describes a computed tomography (CT) apparatus for inspecting (imaging) an inspection object placed on a table while rotating the table. The CT apparatus detects the tilting of the table with the sensor, and determines any positional deviation in an imaging operation. The apparatus described in Patent Literature 1 performs such software correction to prevent deterioration of the image quality caused by unsteady movements of the table.

CITATION LIST

Patent Literature

Patent Literature 1: Japanese Unexamined Patent Application Publication No. 2014-115216

SUMMARY

Technical Problem

However, the technique described in Patent Literature 1 has the issues described below. First, the technique is limited by the accuracy of the sensor. A sensor with insufficient accuracy cannot achieve effective correction. The inspection apparatus may use an additional sensor for any additional movable component. Additionally, the technique, which is applicable to an apparatus including a turnable table, is not applicable to an apparatus including stages with multiple axes, such as XY stages or XYZ stages. This is because the stages with multiple axes can have positional deviations caused by positioning errors along the axes, instead of unsteady movements of the entire stages.

In response to the above issues, one or more aspects of the present invention are directed to a technique having wide applications at low cost in an X-ray inspection apparatus that reduces deterioration of the quality of three-dimensional data caused by repeatability error.

Solution to Problem

In response to the above issue, an X-ray inspection apparatus according to a first aspect of the present invention includes an X-ray inspection apparatus for capturing multiple sets of image data for an inspection object while a position of the inspection object is being changed relative to an X-ray source and an X-ray camera, and reconstructing three-dimensional data for the inspection object using the image data. The apparatus includes a stage that moves at least one of the inspection object, the X-ray source, and the X-ray camera by driving a motor, a position detection unit that periodically obtains a position detection value of the motor, and stores the position detection value in association with time, an imaging timing obtaining unit that stores an imaging timing at which imaging is performed by the X-ray camera in association with time, an imaging position calculation unit that calculates relative positions of the inspection object, and the X-ray source and the X-ray camera corresponding to the imaging timing using the position detection value of the motor obtained at the imaging timing, and a reconstruction unit that performs a reconstruction process using image data captured by the X-ray camera and the relative positions in the image data at the imaging timing.

The stage moves at least one of the inspection object, the X-ray source, and the X-ray camera by driving the motor. Typically, the inspection object is fixed and the X-ray source and the X-ray camera are moved, or the X-ray source and the X-ray camera are fixed and the inspection object is moved. The position detection value of the motor can be obtained from, for example, an encoder included in the motor. The position detection unit stores (accumulates) the position detection value of the motor in association with the detection time.

The imaging position calculation unit calculates the real coordinates of the inspection object, the X-ray source, and the X-ray camera using design information, and determines the relative positions of the inspection object, the X-ray source, and the X-ray camera. The imaging position calculation unit may correct, using preliminary obtained calibration information, the relative positions that are determined using the design information and the position detection value of the motor. An actual apparatus deviates from its design information due to manufacturing errors, and thus may perform correction using such calibration information.

In the X-ray inspection apparatus according to the above aspect of the invention, the inspection object may be fixed, and the stage may move the X-ray source and the X-ray camera. The stage may include XY stages or XYZ stages. In the X-ray inspection apparatus according to the above aspect of the invention, the X-ray source and the X-ray camera may be fixed, and the stage may move the inspection object. In this case, the stage may be a turnable stage.

An X-ray inspection apparatus according to another aspect of the invention may include at least one of the above units. An X-ray inspection method according to another aspect of the invention may include at least one of the processes performed by the above units. A computer program for enabling a computer to implement the steps included in the method, and a computer-readable non-transitory storage medium storing the program may also fall within the scope of the invention. The above structure and processes may be combined with one another unless any technical contradiction arises.

Advantageous Effects

The X-ray inspection apparatus according to one or more embodiments of the present invention can reduce deterioration of the quality of three-dimensional data caused by repeatability error without increasing the cost or without limiting the apparatus structure.

DETAILED DESCRIPTION

Embodiments of the present invention will now be described in detail by way of example with reference to the drawings. The dimensions, materials, shapes, and relative positions of the components described in the embodiments do not intend to limit the scope of the present invention, unless otherwise specified.

First Embodiment

Overview

Figure 1:
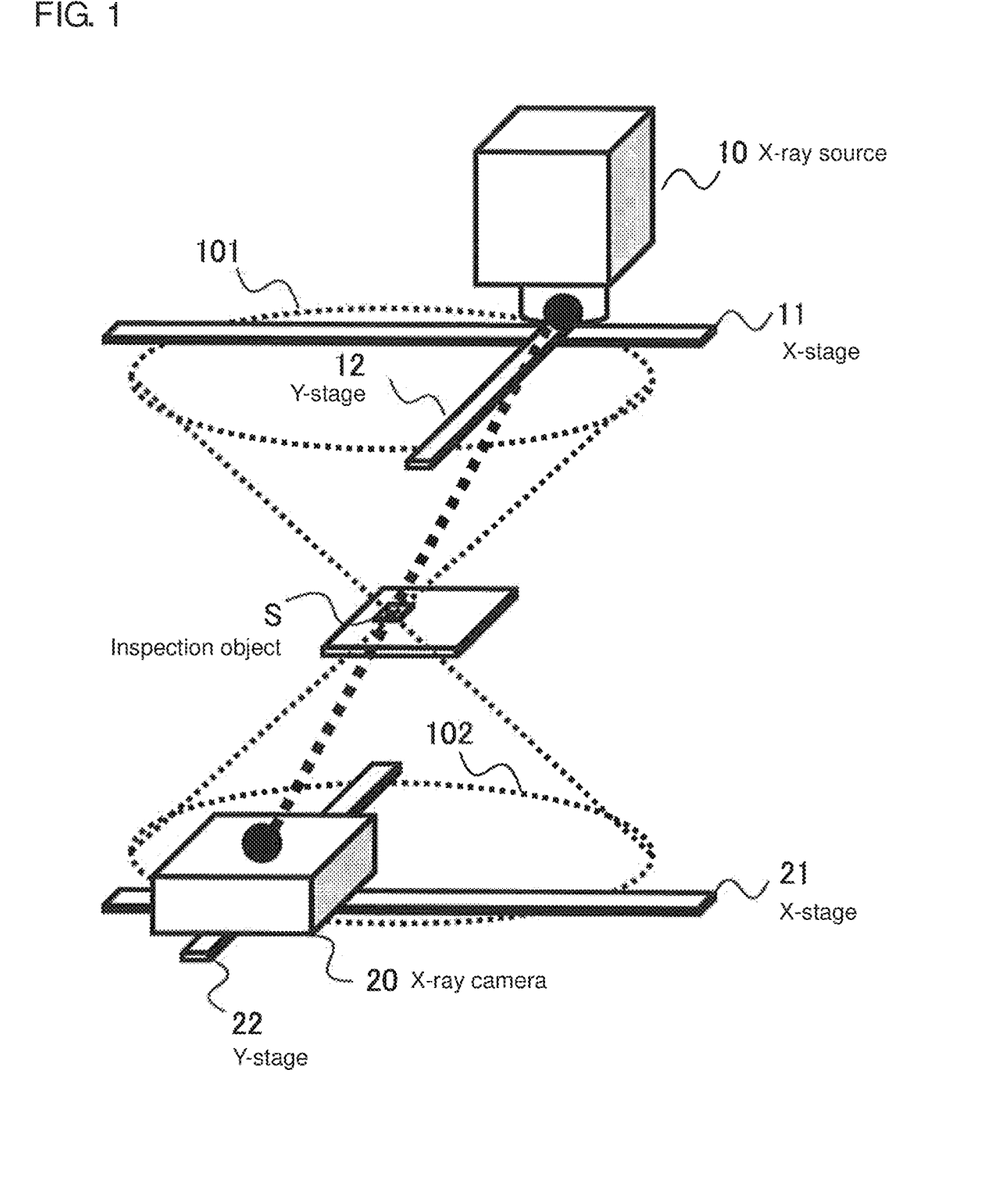
FIG. 1 is a diagram showing an overview of an X-ray inspection apparatus according to a first embodiment.

FIG. 1 shows an overview of an X-ray inspection apparatus according to a first embodiment of the present invention. The X-ray inspection apparatus captures images of an inspection object S that is transported on a transport roller from multiple imaging positions to obtain three-dimensional data. More specifically, the X-ray inspection apparatus irradiates the inspection object S with X-rays emitted from an X-ray source 10, and captures an image of the transmitted X-rays with an X-ray camera 20. The X-ray source 10 is movable with an X-stage 11 and a Y-stage 12. The X-ray camera 20 is movable with an X-stage 21 and a Y-stage 22. On these stages, the X-ray source 10 moves on a circular path 101, and the X-ray camera 20 moves on a circular path 102 to allow imaging of the object S at multiple positions on the paths.

Structure and Processing

Figure 2:
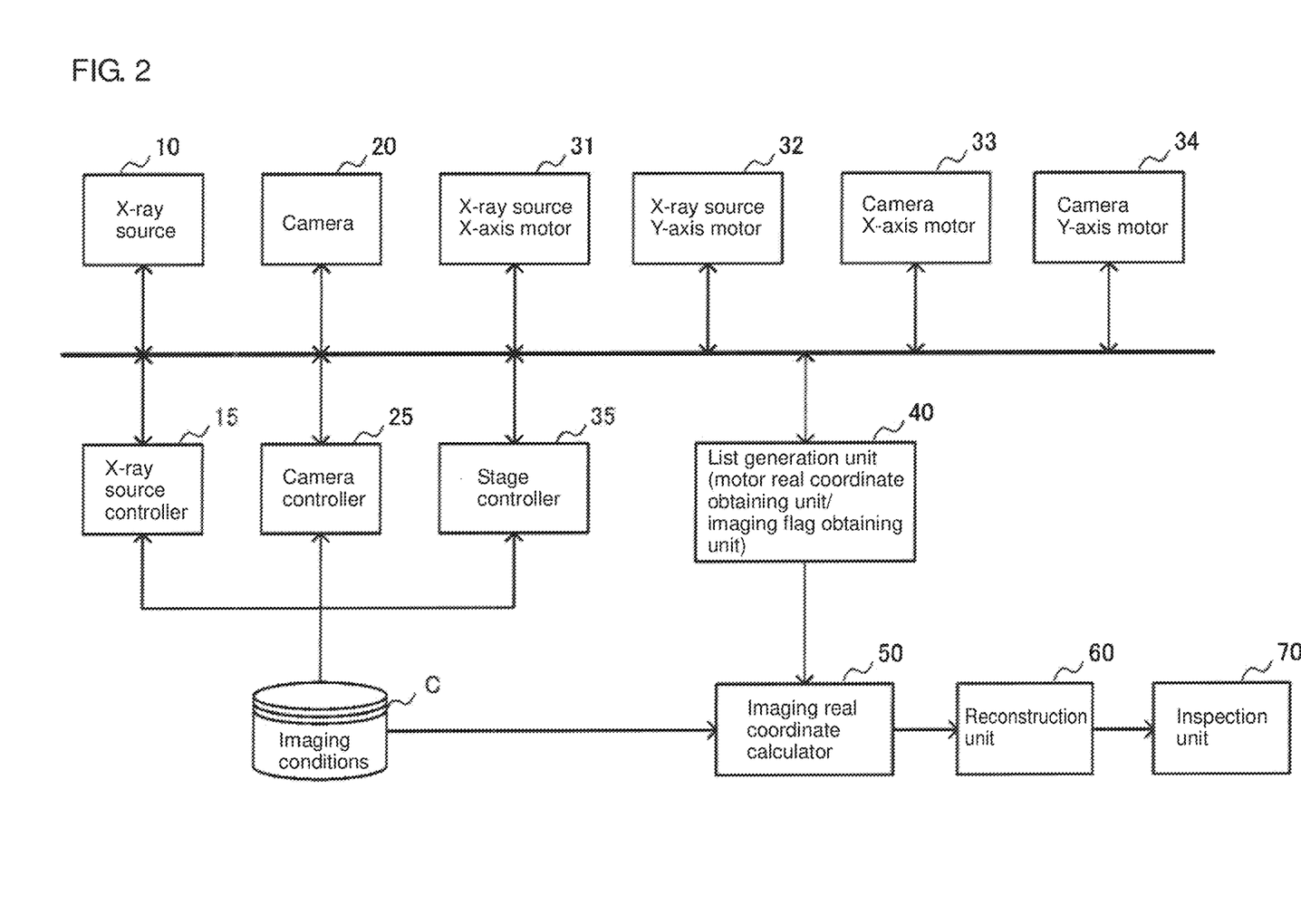
FIG. 2 is a block diagram of the X-ray inspection apparatus according to the first embodiment.

FIG. 2 is a block diagram of the X-ray inspection apparatus. The X-ray inspection apparatus includes the X-ray source 10, the X-ray camera 20 (hereafter simply the camera), an X-axis motor 31 for the X-ray source, a Y-axis motor 32 for the X-ray source, a camera X-axis motor 33, a camera Y-axis motor 34, an imaging condition storage unit C, an X-ray source controller 15, a camera controller 25, a stage controller 35, a list generation unit 40, an imaging real coordinate calculator 50, a reconstruction unit 60, and an inspection unit 70. These functional units will be described together with the processing described with reference to FIG. 3.

The functional units including the X-ray source controller 15, the camera controller 25, the stage controller 35, the list generation unit 40, the imaging real coordinate calculator 50, the reconstruction unit 60, and the inspection unit 70 each may be implemented using a logic circuit such as an application specific integrated circuit (ASIC) or a field programmable gate array (FPGA), or using a computer including a general-purpose microprocessor and a memory that stores programs.

Figure 3:
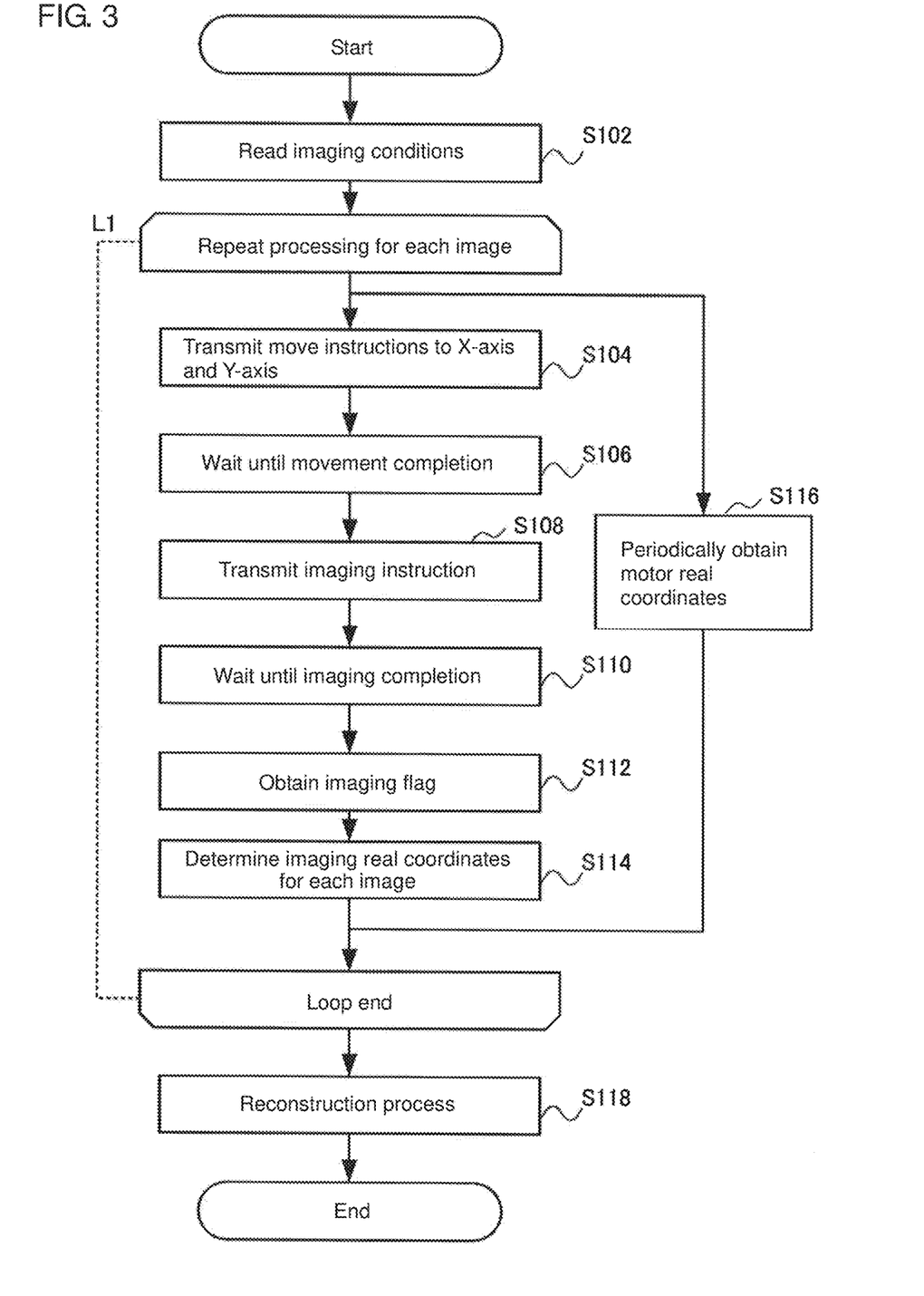
FIG. 3 is a flowchart showing an X-ray inspection process according to the first embodiment.

FIG. 3 is a flowchart showing an inspection process performed by the X-ray inspection apparatus according to the present embodiment.

In step S102, the X-ray inspection apparatus reads imaging conditions from the imaging condition storage unit C. The imaging conditions include the number of images to be captured per inspection, the camera exposure time, and the positions of the X-ray source 10 and the camera 20 in each imaging operation.

The imaging conditions include the conditions described below.

Number of images to be captured: 32

Camera exposure time: 50 milliseconds

The X-ray source position (200, 300) and the camera position (50, 50) for the first image The X-ray source position (300, 300) and the camera position (30, 30) for the second image The processing of a loop L1 is repeatedly performed for each captured image.

During this loop processing, the list generation unit 40 periodically obtains a position detection value of the motor for each stage, and stores the obtained value in association with the detection time (step S116). The list generation unit 40 obtains position detection values (read values) detected by encoders included in the X-ray source X-axis motor 31, the X-ray source Y-axis motor 32, the camera X-axis motor 33, and the camera Y-axis motor 34. These position detection values obtained from the motors can be used to determine the positions of the X-ray source 10 and the camera 20.

The list generation unit 40 stores the positions of the X-ray source 10 and the camera 20, which are determined using the read values of the motors (encoders). The read values of the motors can be converted to the positions of the X-ray source 10 and the camera 20 using design information (e.g., stage arrangement information). Thus, the list generation unit 40 may store the read values of the motors. The positions of the X-ray source 10 and the camera 20, which are determined using the position detection values obtained by the encoders, represent the actual positions of the X-ray source 10 and the camera 20. This position of the X-ray source 10 or the camera 20, corresponding to the coordinates of the actual position of the X-ray source 10 or the camera 20 determined using the position values detected by the motors, will be referred to as the motor real coordinates of the X-ray source 10 or the camera 20. The list generation unit 40 thus functions as a motor real coordinate obtaining unit that periodically obtains the motor real coordinates.

The list generation unit 40 may obtain the motor real coordinates at appropriate time intervals determined based on the intended temporal resolution or the permissible amount of data to be transmitted. The time interval may be, for example, 1 millisecond or 10 milliseconds.

The list generation unit 40 may not store all the obtained motor real coordinates, but may store values obtained at timings close to the imaging timing.

The processing in steps S104 to S114 in the loop L1 will now be described. In step S104, the X-ray inspection apparatus transmits move instructions to the stage controller 35 to move the X-ray source 10 and the camera 20 to the positions defined by the imaging conditions (hereafter, the imaging positions). More specifically, the stage controller 35 transmits a move instruction to the X-ray source X-axis motor 31 and the X-ray source Y-axis motor 32 to move the X-ray source 10 to the imaging position, and transmits a move instruction to the camera X-axis motor 33 and the camera Y-axis motor 34 to move the camera 20 to the imaging position.

In step S106, the X-ray inspection apparatus waits until the movement is complete. The completion of the movement may be determined with any method. For example, the movement may be determined to be complete at the timing when a movement completion signal is received from the motors. The movement may be determined to be complete when the motor real coordinates that are being monitored fall within a predetermined range (e.g., a range of ±n micrometers from a target position). The movement may be determined to be complete when a predetermined time in accordance with the moving distance passes after the move instruction is transmitted.

When determining the completion of the stage movement, the X-ray inspection apparatus transmits an imaging instruction in step S108. In response to the imaging instruction, the X-ray source controller 15 controls the X-ray source 10 to irradiate the inspection object S with X-rays, and the camera controller 25 controls the camera 20 to perform exposure and to obtain image data. The image data is stored into the memory.

In step S110, the X-ray inspection apparatus waits until the imaging operation is complete. The completion of the imaging operation may be determined with any method. For example, the movement may be determined to be complete at the timing when an imaging completion signal is received from the camera 20. The movement may be determined to be complete when the exposure time defined by the imaging conditions passes after the imaging instruction is transmitted.

When the stage (the X-ray source 10 or the camera 20) moves on a regular path at a constant speed for imaging performed at constant time intervals, the operation for each imaging operation including transmitting move instructions, waiting for completion of the movement, transmitting an imaging instruction, and waiting for completion of the imaging operation may be eliminated. In this case, the imaging operation may be performed at regular time intervals in accordance with the moving distance of the stage, while the stage is being controlled to move on the above path. For example, the stages may be moved on a straight path or a circular path at a constant speed for imaging performed at constant time intervals of 100 milliseconds.

In step S114, the list generation unit 40 obtains an imaging flag (an imaging completion signal) indicating completion of the imaging operation from the camera 20, and stores the imaging flag in association with the time at which the imaging flag is obtained. The list generation unit 40 thus functions as an imaging flag obtaining unit. Although the imaging flag is obtained after the imaging operation is complete (after step S110) in the flowchart, the imaging flag may be obtained in parallel during the waiting period from when the imaging instruction is transmitted to when the imaging is complete.

Figure 4:
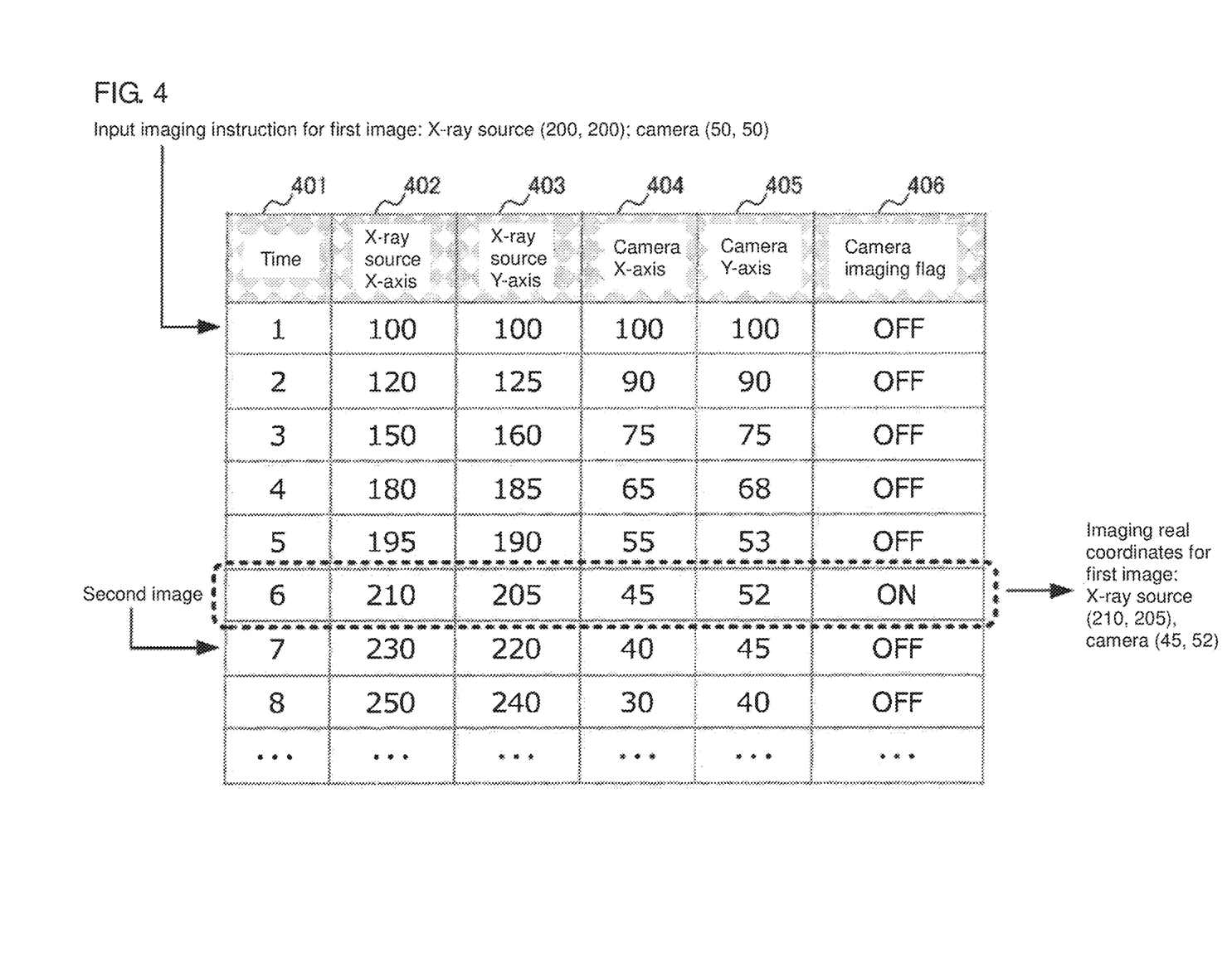
FIG. 4 is a table storing motor real coordinates and camera imaging flags.

The list generation unit 40 periodically obtains the motor real coordinates of the X-ray source 10 and the camera 20, and thus can obtain the motor real coordinates of the X-ray source 10 and the camera 20 at the timing when an imaging flag is obtained. FIG. 4 is a table storing the motor real coordinates of the X-ray source 10 and the camera 20 and the imaging flags in correspondence with the times. The table in FIG. 4 includes a time field 401 storing the time obtained from a system clock (not shown), and an X-axis field 402 for the X-ray source, a Y-axis field 403 for the X-ray source, a camera X-axis field 404, and a camera Y-axis field 405 each storing the motor real coordinates obtained from the corresponding motor, and a camera imaging flag field 406 storing the on or off state of an imaging flag obtained from the camera 20.

When an imaging operation is performed, the imaging real coordinate calculator 50 obtains the corresponding actual positions of the X-ray source 10 and the camera 20 from the list in FIG. 4. This position of the X-ray source 10 or the camera 20, which corresponds to the coordinates of the actual position of the X-ray source 10 or the camera 20 when the imaging operation is performed, will be referred to as the imaging real coordinates of the X-ray source 10 or the camera 20.

Although the first imaging operation is instructed to be performed with the X-ray source 10 at the position (200, 200) and the camera 20 at the position (50, 50), the list in FIG. 4 reveals that the actual imaging operation is performed with the X-ray source 10 at the position (210, 205) and the camera 20 at the position (45, 52).

The imaging flag for the camera may be output at different timings depending on the specifications of the camera or the control board for the camera. For example, the imaging flag may be output when the imaging operation is started or when the imaging operation is complete, or may be output continuously during the imaging operation (exposure). The imaging real coordinate calculator 50 may thus determine the imaging real coordinates of the X-ray source 10 or the camera 20 to reflect these specifications. In particular, when the time interval for obtaining the motor real coordinates is shorter than the exposure time, the imaging real coordinate calculator 50 may use the average position during the exposure as the imaging real coordinates.

Figure 5A:
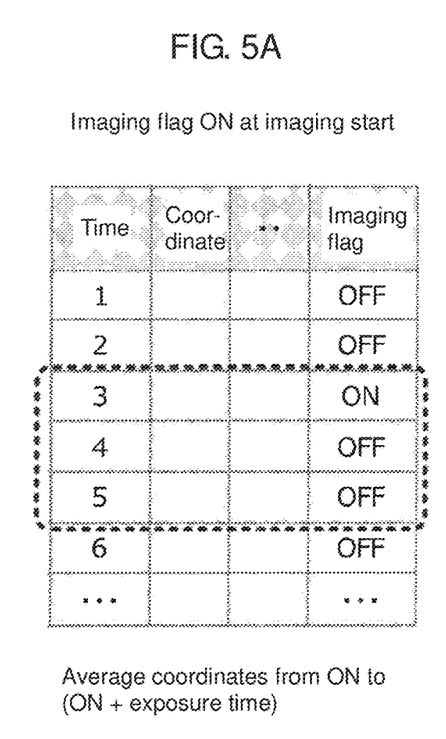
FIGS. 5A to 5C are tables each showing a method for calculating the imaging positions for a different state of an imaging flag.
Figure 5B:
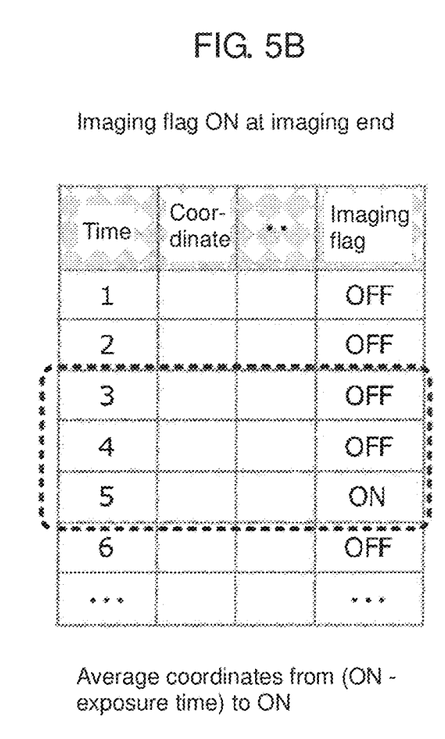
Figure 5C:
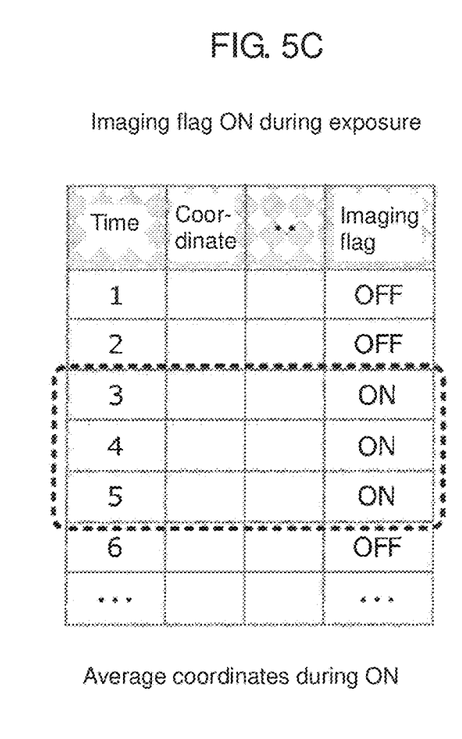

FIG. 5A is a table listing cases in which the imaging flag is set on when the imaging operation is started. In these cases, the average coordinates in the period from when the imaging flag is set on to when the exposure time passes may be used as the imaging real coordinates. FIG. 5B is a table listing cases in which the imaging flag is set on when the imaging operation is complete. In these cases, the average coordinates during the exposure time before the imaging flag is set on may be used as the imaging real coordinates. FIG. 5C is a table listing cases in which the imaging flag continues to be on during the imaging operation. In these cases, the average coordinates in the period in which the imaging flag continues to be on may be used as the imaging real coordinates.

Although the imaging real coordinates of the X-ray source 10 and the camera 20 are obtained for every imaging operation in the flowchart shown in FIG. 3, all imaging operations may be performed first, and then the imaging real coordinates may be obtained for each of the captured images. The list generation unit 40 may not store all the position detection values obtained from the motors. The technique according to the present embodiment may simply use the position detection value obtained at the imaging timing. The list generation unit 40 may thus simply store the position detection values obtained at timings close to the imaging timing, and may delete the position detection values obtained at any other timings that are not close to the imaging timing.

When all the imaging operations are complete, the reconstruction unit 60 performs a reconstruction process in step S118 using the image data and the imaging real coordinates resulting from each imaging operation to obtain three-dimensional data for the inspection object S. The reconstruction process is known, and thus will not be described.

When the three-dimensional data for the inspection object S is obtained, the inspection unit 70 determines whether the inspection object S is normal or abnormal based on the obtained data. The inspection unit 70 determines whether the inspection object has been manufactured as designed. The three-dimensional data obtained using X-rays can reveal defects on internal layers in addition to surface defects.

Advantageous Effects of Present Embodiment

Although the stages are moved toward their intended positions (instructed positions) with the stage controller 35, the actual positions of the moved stages can deviate from the intended positions due to positioning errors. The apparatus according to the present embodiment periodically obtains the position detection values of the stages (motors) for moving the X-ray source 10 and the camera 20, and determines the positions of the X-ray source 10 and the camera 20 during the imaging operation using the position detection values of the stages obtained at the imaging timing. The position detection values obtained from the motors have high accuracy in units of, for example, 0.1 micrometers. The accurate information is used to determine the actual positions of the X-ray source 10 and the camera 20 with high accuracy. The reconstruction process uses the actual positions obtained from the motors for their stages, instead of using the instructed positions. Thus, three-dimensional data with high quality can be obtained, independently of any positional deviations (repeatability error) of the stages.

The technique according to the present embodiment is applicable to, in addition to the X-ray inspection apparatus including XY stages, an X-ray inspection apparatus including XYZ stages or including a turnable stage (a turntable). The technique has a wide range of applications.

The technique according to the present embodiment obtains the detection positions from the motors, and thus uses no additional sensors for any additional movable components. The technique can thus be implemented at low cost.

Modifications

Although the inspection object S is fixed and the X-ray source 10 and the camera 20 are moved in the above embodiment, the X-ray source 10 and the camera 20 may be fixed and the inspection object S may be moved. Typically, the apparatus may have any structure that allows movement of the inspection object S relative to the X-ray source 10 and the camera 20. The position detection values of the movable units (stages) are periodically obtained to determine the relative positions of the inspection object S, and the X-ray source 10 and the camera 20 at the imaging timing. The structure of this modification also reconstructs three-dimensional data with high quality, independently of any positional deviations between the intended imaging positions and the actual imaging positions in the same manner as described above.

Although the motor real coordinates are directly obtained from the motors in the above embodiment, the motor real coordinates may be indirectly obtained through a motor driver or a programmable logic controller (PLC). The imaging flag may also be indirectly obtained through a camera control board or a PLC, instead of being directly obtained from the camera.

Second Embodiment

Figure 6:
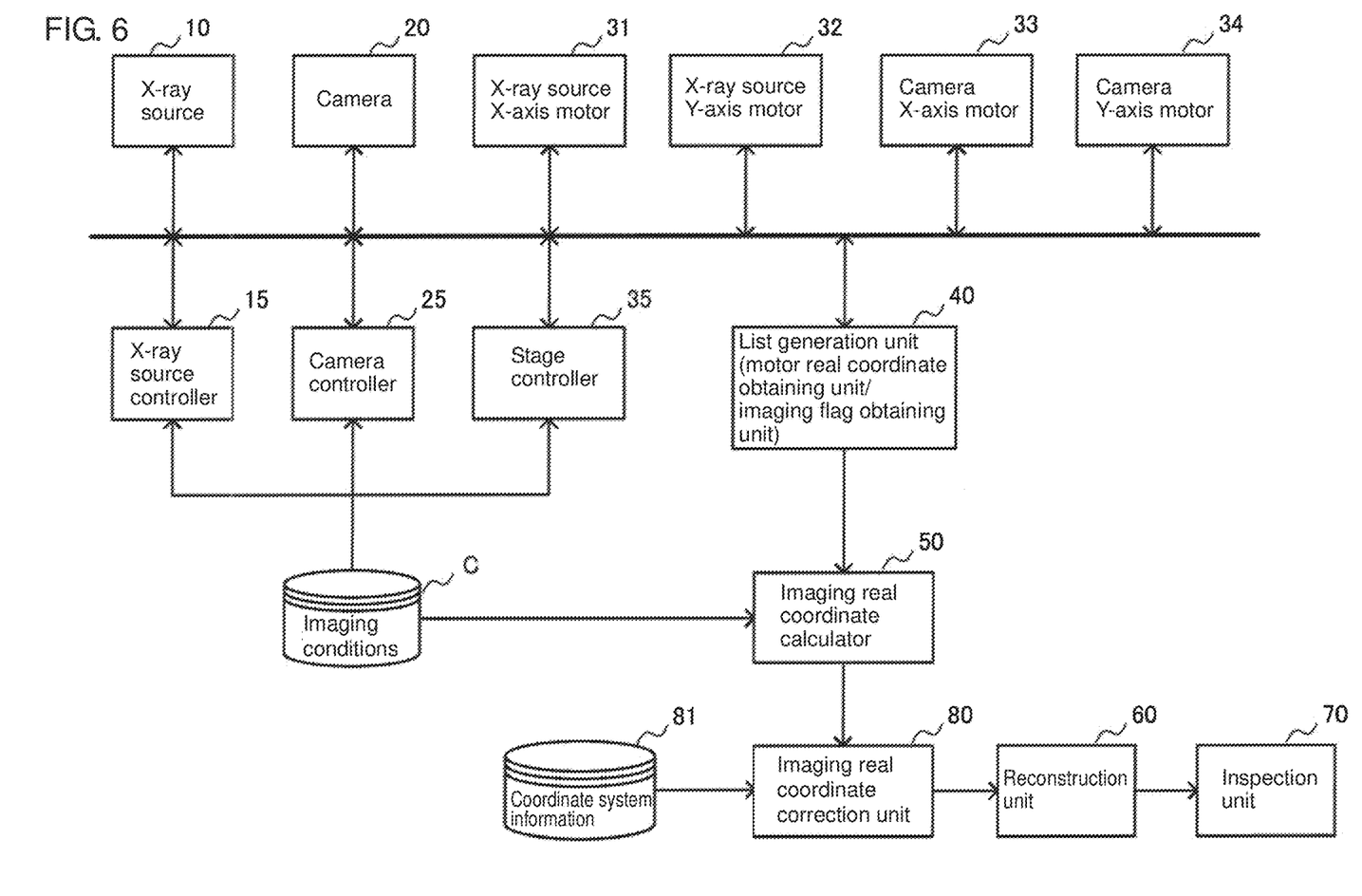
FIG. 6 is a block diagram of an X-ray inspection apparatus according to a second embodiment.
Figure 7:
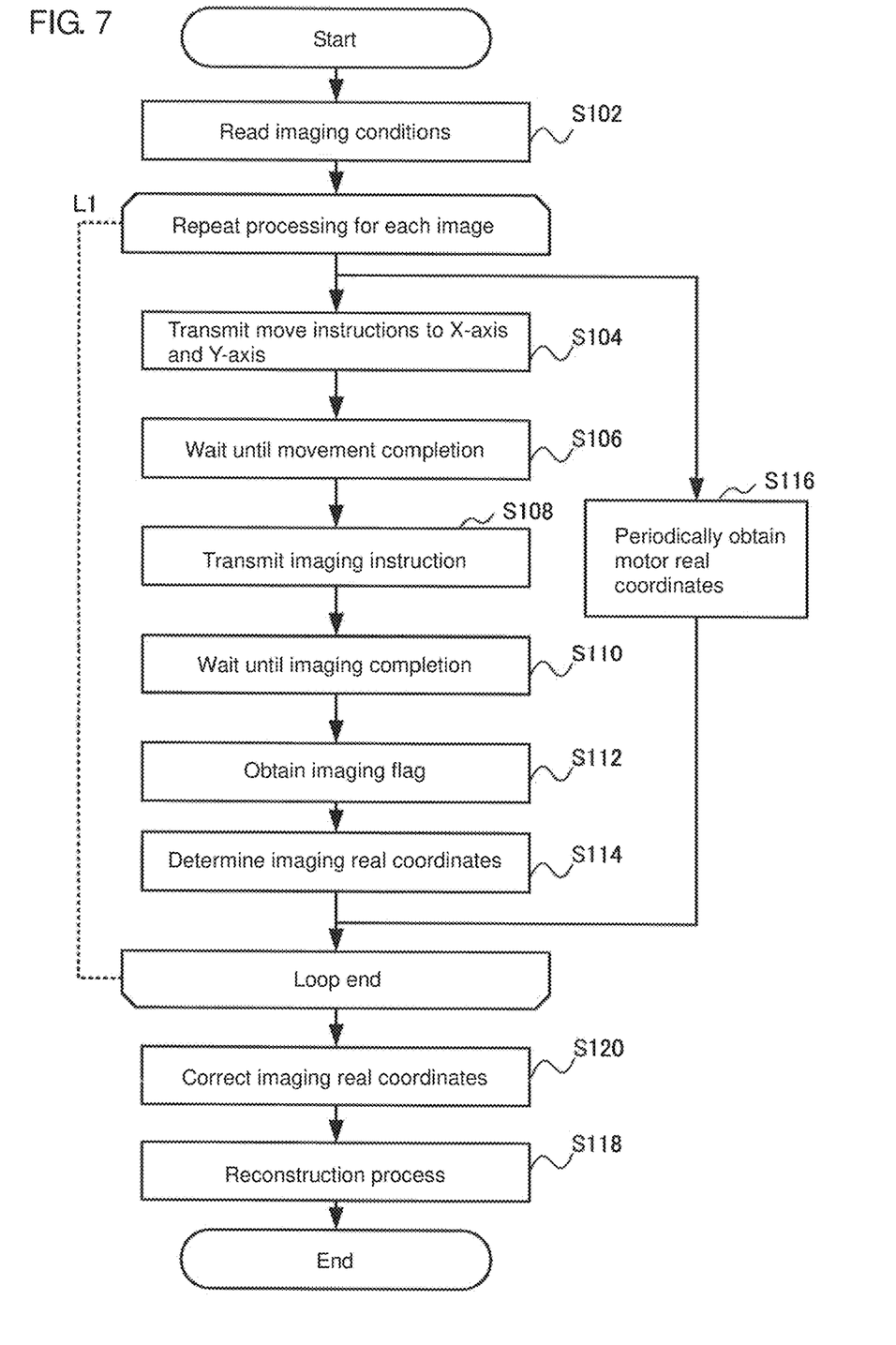
FIG. 7 is a flowchart showing an X-ray inspection process according to the second embodiment.

FIG. 6 is a block diagram of an X-ray inspection apparatus according to a second embodiment. FIG. 7 is a flowchart showing an inspection process according to the second embodiment. The X-ray inspection apparatus according to the present embodiment differs from the apparatus according to the first embodiment in its additional components and process, namely an imaging real coordinate correction unit 80 and a coordinate system information storage unit 81, and step S120 for correcting the imaging real coordinates preceding the reconstruction process in S118. The second embodiment will be described focusing on the differences from the first embodiment.

The positions of an X-ray source 10 and a camera 20 obtained from the position detection values of the motors for their stages may not completely match the actual positions of the X-ray source 10 and the camera 20. For example, although the position detection value of the X-stage of the XY stages indicates the X-coordinate of the X-ray source 10 or the camera 20, the X-stage may not actually match the X-axis completely, and the position detection value obtained from the motor for the stage can deviate from the actual position. The X-axis and the Y-axis are orthogonal to each other when designed, but can vary within a predetermined range (e.g., from 89.9 to 90.1 degrees) in manufactured products. Improving the manufacturing accuracy will increase the cost. Designing all the axes with high accuracy will increase the cost of the X-ray inspection apparatus.

To respond to this, the apparatus of the present embodiment uses an additional process for correcting the imaging real coordinates to generate higher quality three-dimensional data than in the first embodiment.

For this correction process, differences between the detection coordinates obtained from the motor and the actual space coordinates are measured preliminary, and are stored into the coordinate system information storage unit 81. Such differences may be obtained with any known method used in calibrating the coordinate systems. One example will now be described.

Figure 8A:
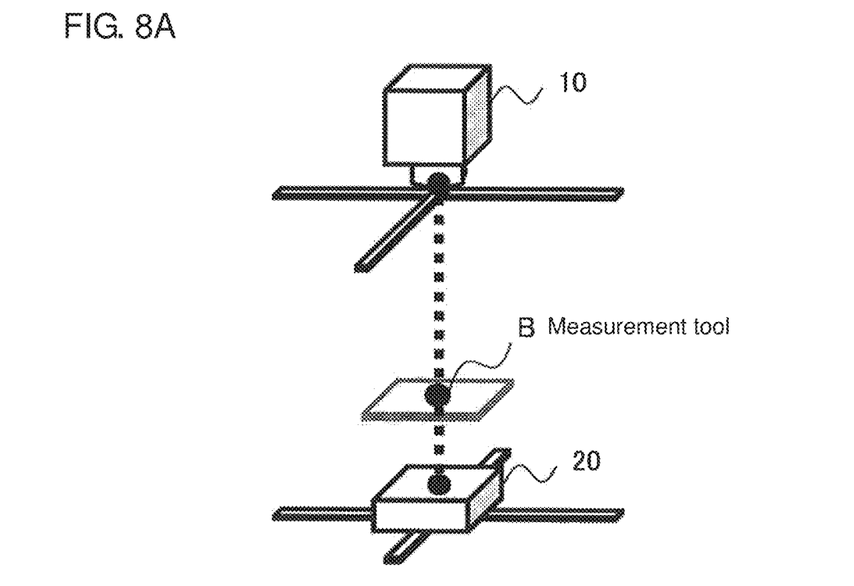
FIGS. 8A and 8B are diagrams describing a method for determining differences (coordinate system information) between a motor coordinate system and a space coordinate system.

As shown in FIG. 8A, the X-ray source 10 and the camera 20 are first positioned to place a measurement tool B in the center of the camera view of the camera 20. The relative positional deviations between the axes can be calculated using the coordinates in this positioning.

Figure 8B:
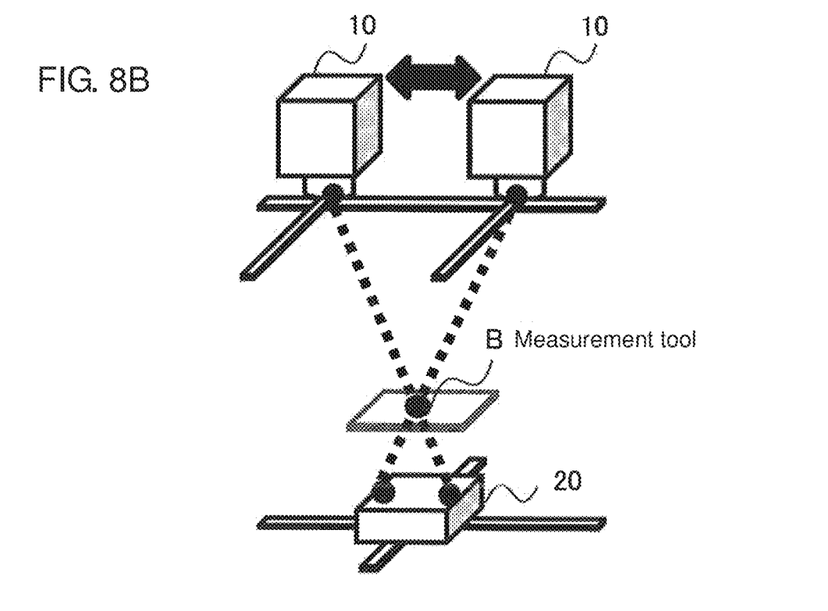

As shown in FIG. 8B, images of the measurement tool B are then captured for each axis, with the target axis moving and the other axis fixed. For example, when the X-ray source 10 has the X-axis angle as designed, the tool will move only in X-direction in the captured images. Any movement of the tool in Y-direction in the captured images indicates that the X-axis of the X-ray source has an angular deviation relative to the camera. As described above, changes in the positions of the measurement tool B in the captured images before and after the movement can be used to calculate the relative angular deviations between the axes.

The imaging real coordinate correction unit 80 corrects the coordinates for each captured image obtained by the imaging real coordinate calculator 50 in accordance with the differences stored in the coordinate system information storage unit 81. The actual positions of the X-ray source 10 and the camera 20 during the imaging operation can thus be determined with higher accuracy. The reconstruction unit 60 reconstructs the data using such highly accurate positional information. This improves the quality of the resulting three-dimensional data further.

REFERENCE SIGNS LIST

S inspection object
10 X-ray source
20 X-ray camera
40 list generation unit
50 imaging real coordinate calculator
60 reconstruction unit
70 inspection unit

The invention claimed is:

1. An X-ray inspection apparatus for capturing multiple sets of image data for an inspection object while a position of the inspection object is being changed relative to an X-ray source and an X-ray camera, and reconstructing three-dimensional data for the inspection object using the image data, the apparatus comprising:
    a stage configured to move the X-ray source and the X-ray camera by driving a motor; and
    a processor configured with a program to perform operations comprising:
        operation as a position detection unit configured to periodically obtain a position of the X-ray source and store the position of the X-ray source in association with time, and obtain a position of the X-ray camera and store the position of the X-ray camera in association with time;
        operation as an imaging timing obtaining unit configured to store, in association with time, an imaging timing at which imaging is performed by the X-ray camera;
        operation as an imaging position calculation unit configured to:
            calculate relative positions of the inspection object, the X-ray source, and the X-ray camera corresponding to the imaging timing using the stored position of the X-ray source and the stored position of the X-ray camera obtained at the imaging timing;
            determine the relative positions using design information and the stored position of the X-ray source and the stored position of the X-ray camera obtained by the position detection unit; and
            correct the relative positions using preliminary obtained calibration information; and
        operation as a reconstruction unit configured to perform a reconstruction process using image data captured by the X-ray camera and the relative positions in the image data at the imaging timing.

2. The X-ray inspection apparatus according to claim 1, wherein
    the inspection object is fixed.

3. An X-ray inspection method used in an X-ray inspection apparatus for capturing multiple sets of image data for an inspection object while a position of the inspection object is being changed relative to an X-ray source and an X-ray camera, and reconstructing three-dimensional data for the inspection object using the image data, the method comprising:
    periodically obtaining a position of the X-ray source and a position of the X-ray camera;
    storing the position of the X-ray source in association with time and the position of the X-ray camera in association with time;
    capturing multiple images of the inspection object with the X-ray camera while a position of the inspection object is being changed relative to the X-ray source and the X-ray camera;
    storing an imaging timing at which imaging is performed by the X-ray camera;
    calculating relative positions of the inspection object, the X-ray source, and the X-ray camera corresponding to the imaging timing using the stored position of the X-ray source and the stored position of the X-ray camera obtained at the imaging timing;
    determining the relative positions using design information and the stored position of the X-ray source and the stored position of the X-ray camera;
    correcting the relative positions using preliminary obtained calibration information; and
    performing a reconstruction process using image data captured by the X-ray camera and the relative positions in the image data at the imaging timing.

4. A non-transitory computer-readable storage medium storing a program for enabling a computer to implement the steps included in the method according to claim 3.

5. The method according to claim 3, wherein calculating the relative positions of the inspection object, the X-ray source, and the X-ray camera corresponding to the imaging timing comprises calculating the relative positions of the inspection object, the X-ray source, and the X-ray camera corresponding to the imaging timing based on design information, the stored position of the X-ray source, and the stored position of the X-ray camera.

6. The method according to claim 5, further comprising correcting the relative positions using preliminary obtained calibration information.

7. The method according to claim 3, wherein the inspection object is fixed.

\* \* \* \* \*